United States Patent
Carrascoso et al.

(10) Patent No.: US 11,624,750 B2
(45) Date of Patent: *Apr. 11, 2023

(54) IDENTIFICATION AND USE OF GLYCOPEPTIDES AS BIOMARKERS FOR DIAGNOSIS AND TREATMENT MONITORING

(71) Applicant: Venn Biosciences Corporation, South San Francisco, CA (US)

(72) Inventors: Aldo Mario Eduardo Silva Carrascoso, Daly City, CA (US); Carolyn Ruth Bertozzi, Menlo Park, CA (US); Carlito Bangeles Lebrilla, Davis, CA (US); Lieza Marie Araullo Danan-Leon, S. San Francisco, CA (US)

(73) Assignee: Venn Biosciences Corporation, South San Francisco, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 17/067,460

(22) Filed: Oct. 9, 2020

(65) Prior Publication Data
US 2021/0208159 A1 Jul. 8, 2021

Related U.S. Application Data

(63) Continuation of application No. 16/120,016, filed on Aug. 31, 2018, now Pat. No. 10,837,970.
(Continued)

(51) Int. Cl.
*G01N 33/68* (2006.01)
*G16B 20/00* (2019.01)
(Continued)

(52) U.S. Cl.
CPC ....... *G01N 33/6857* (2013.01); *G01N 33/564* (2013.01); *G01N 33/57415* (2013.01);
(Continued)

(58) Field of Classification Search
CPC ............. G01N 33/6857; G01N 33/564; G01N 33/57415; G01N 33/6842; G01N 33/6848;
(Continued)

(56) References Cited

U.S. PATENT DOCUMENTS 7,031,845 B2 4/2006 Scott et al.
7,298,474 B2 11/2007 Drachev et al.
(Continued)

FOREIGN PATENT DOCUMENTS

AU 2008202217 A1 6/2008
AU 2015100100 A4 3/2015
(Continued)

OTHER PUBLICATIONS

An et al., "Profiling of glycans in serum for the discovery of potential biomarkers for ovarian cancer", Journal of Proteome Research, American Chemical Society 5(7): 1626-1635 (2006).
(Continued)

*Primary Examiner* — Christine T Mui
(74) *Attorney, Agent, or Firm* — Morrison & Foerster LLP (57) ABSTRACT

Provided herein are methods for identifying new biomarkers for various diseases using proteomics, peptidomics, metabolics, proteoglycomics, glycomics, mass spectrometry and machine learning. The present disclosure also provides glycopeptides as biomarkers for various diseases such as cancer and autoimmune diseases.

24 Claims, 6 Drawing Sheets

Related U.S. Application Data (60) Provisional application No. 62/553,676, filed on Sep. 1, 2017.

(51) Int. Cl.
| | | |
|---|---|---|
| *G16B 40/00* | (2019.01) | |
| *G01N 33/564* | (2006.01) | |
| *G16B 40/20* | (2019.01) | |
| *G01N 33/574* | (2006.01) | |
| *G16B 40/10* | (2019.01) | |

(52) U.S. Cl.
CPC ..... *G01N 33/6842* (2013.01); *G01N 33/6848* (2013.01); *G16B 20/00* (2019.02); *G16B 40/00* (2019.02); *G16B 40/10* (2019.02); *G16B 40/20* (2019.02); *G01N 2400/00* (2013.01); *G01N 2800/08* (2013.01)

(58) Field of Classification Search
CPC ........... G01N 2400/00; G01N 2800/08; G01N 2560/00; G16B 20/00; G16B 40/00; G16B 40/10; G16B 40/20
USPC ........................................................ 436/173
See application file for complete search history.

(56) References Cited

U.S. PATENT DOCUMENTS

| | | | |
|---|---|---|---|
| 8,163,896 | B1 | 4/2012 | Bentwich |
| 8,207,316 | B1 | 6/2012 | Bentwich |
| 8,288,110 | B2 | 10/2012 | Lopez et al. |
| 8,313,950 | B2 | 11/2012 | Rovin et al. |
| 8,497,066 | B2 | 7/2013 | Levenson et al. |
| 8,731,839 | B2 | 5/2014 | Bhanot et al. |
| 8,921,053 | B2 | 12/2014 | Siu et al. |
| 9,274,118 | B2 | 3/2016 | Mansfield et al. |
| 9,335,331 | B2 | 5/2016 | Lee et al. |
| 9,459,258 | B2 | 10/2016 | Tang et al. |
| 9,846,158 | B2 | 12/2017 | Mansfield et al. |
| 9,921,210 | B2 | 3/2018 | Collins et al. |
| 9,968,666 | B2 | 5/2018 | Lu et al. |
| 10,837,970 | B2 * | 11/2020 | Carrascoso ............ G16B 40/10 |
| 2004/0005634 | A1 | 1/2004 | Patz, Jr. et al. |
| 2004/0043436 | A1 | 3/2004 | Vlahou et al. |
| 2004/0115774 | A1 | 6/2004 | Kochendoerfer et al. |
| 2004/0229283 | A1 | 11/2004 | Gygi et al. |
| 2005/0048547 | A1 | 3/2005 | Zhao et al. |
| 2005/0260678 | A1 | 11/2005 | Tomosugi et al. |
| 2005/0266576 | A1 | 12/2005 | Soykan et al. |
| 2006/0053005 | A1 | 3/2006 | Gulati |
| 2006/0088894 | A1 | 4/2006 | Wright et al. |
| 2006/0127950 | A1 | 6/2006 | Bosques et al. |
| 2006/0141528 | A1 | 6/2006 | Aebersold et al. |
| 2006/0246495 | A1 | 11/2006 | Garrett et al. |
| 2007/0037221 | A1 | 2/2007 | Block et al. |
| 2007/0054329 | A1 | 3/2007 | Fung et al. |
| 2007/0077553 | A1 | 4/2007 | Bentwich |
| 2007/0099251 | A1 | 5/2007 | Zhang et al. |
| 2007/0099930 | A1 | 5/2007 | Dudash et al. |
| 2007/0111257 | A1 | 5/2007 | Kohne |
| 2007/0202539 | A1 | 8/2007 | Aebersold et al. |
| 2008/0026485 | A1 | 1/2008 | Hueber et al. |
| 2008/0071148 | A1 | 3/2008 | Bosques et al. |
| 2008/0118462 | A1 | 5/2008 | Alani et al. |
| 2008/0132420 | A1 | 6/2008 | Lubomirski |
| 2008/0195570 | A1 | 8/2008 | Alsafadi et al. |
| 2008/0261258 | A1 | 10/2008 | Smith et al. |
| 2009/0035801 | A1 | 2/2009 | Goldknopf et al. |
| 2009/0042229 | A1 | 2/2009 | Folkman et al. |
| 2009/0053828 | A1 | 2/2009 | Regnier et al. |
| 2009/0104602 | A1 | 4/2009 | Fernandez-Reyes et al. |
| 2009/0104603 | A1 | 4/2009 | Satomaa et al. |
| 2009/0142332 | A1 | 6/2009 | Ried et al. |
| 2009/0169576 | A1 | 7/2009 | Crea et al. |
| 2009/0203055 | A1 | 8/2009 | Ngantung et al. |
| 2009/0258848 | A1 | 10/2009 | Chakravarti et al. |
| 2009/0317834 | A1 | 12/2009 | Laine et al. |
| 2010/0017356 | A1 | 1/2010 | Degrave et al. |
| 2010/0029006 | A1 | 2/2010 | Rosenblatt et al. |
| 2010/0086948 | A1 | 4/2010 | Gold et al. |
| 2010/0136700 | A1 | 6/2010 | Bilello et al. |
| 2010/0240088 | A1 | 9/2010 | Luider et al. |
| 2010/0273661 | A1 | 10/2010 | Qiu et al. |
| 2010/0280562 | A1 | 11/2010 | Pi et al. |
| 2011/0136166 | A1 | 6/2011 | Semmes et al. |
| 2011/0189680 | A1 | 8/2011 | Keown et al. |
| 2011/0190151 | A1 | 8/2011 | McManus et al. |
| 2011/0208433 | A1 | 8/2011 | Grigorieva et al. |
| 2011/0212104 | A1 | 9/2011 | Beaumont et al. |
| 2011/0224913 | A1 | 9/2011 | Cui et al. |
| 2012/0028268 | A1 | 2/2012 | Kentsis et al. |
| 2012/0053080 | A1 | 3/2012 | Cui et al. |
| 2012/0122113 | A1 | 5/2012 | Prions et al. |
| 2012/0149022 | A1 | 6/2012 | Aw |
| 2012/0171694 | A1 | 7/2012 | Mansfield et al. |
| 2012/0178642 | A1 | 7/2012 | Salomon et al. |
| 2012/0264629 | A1 | 10/2012 | Anderberg et al. |
| 2012/0283123 | A1 | 11/2012 | Sarwal et al. |
| 2013/0005598 | A1 | 1/2013 | Haab et al. |
| 2013/0096023 | A1 | 4/2013 | Rovin et al. |
| 2013/0115237 | A1 | 5/2013 | Lu et al. |
| 2013/0158239 | A1 | 6/2013 | Callewaert et al. |
| 2013/0203061 | A1 | 8/2013 | Kuslich et al. |
| 2013/0261015 | A1 | 10/2013 | Ahn et al. |
| 2013/0267439 | A1 | 10/2013 | Mansfield et al. |
| 2013/0287801 | A1 | 10/2013 | Castronovo et al. |
| 2013/0288912 | A1 | 10/2013 | Borrebaeck et al. |
| 2013/0316921 | A1 | 11/2013 | Cohen et al. |
| 2014/0037658 | A1 | 2/2014 | Nilsson et al. |
| 2014/0080138 | A1 | 3/2014 | Ralhan et al. |
| 2014/0148348 | A1 | 5/2014 | Kuslich et al. |
| 2014/0162370 | A1 | 6/2014 | Ling et al. |
| 2014/0322732 | A1 | 10/2014 | Krek et al. |
| 2014/0343451 | A1 | 11/2014 | Pannell et al. |
| 2014/0364341 | A1 | 12/2014 | Mansfield et al. |
| 2015/0057169 | A1 | 2/2015 | Siu et al. |
| 2015/0160233 | A1 | 6/2015 | Tang et al. |
| 2015/0265687 | A1 | 9/2015 | Geldhof et al. |
| 2015/0376723 | A1 | 12/2015 | Keshavjee et al. |
| 2016/0003838 | A1 | 1/2016 | Roedder et al. |
| 2016/0069884 | A1 | 3/2016 | Zhang et al. |
| 2016/0109437 | A1 | 4/2016 | Cooper et al. |
| 2016/0146831 | A1 | 5/2016 | Hueber et al. |
| 2016/0350477 | A1 | 12/2016 | McHugh |
| 2016/0369350 | A1 | 12/2016 | Kassis |
| 2016/0370374 | A1 | 12/2016 | Bosques et al. |
| 2017/0002095 | A1 | 1/2017 | Satomaa et al. |
| 2017/0010265 | A1 | 1/2017 | Kas |
| 2017/0010269 | A1 | 1/2017 | Pennington et al. |
| 2017/0016913 | A1 | 1/2017 | Price et al. |
| 2017/0029888 | A1 | 2/2017 | Cargill et al. |
| 2017/0030904 | A1 | 2/2017 | Liu et al. |
| 2017/0052200 | A1 | 2/2017 | Bulik et al. |
| 2017/0161441 | A1 | 6/2017 | Bilello |
| 2017/0176441 | A1 | 6/2017 | Blume et al. |
| 2017/0205427 | A1 | 7/2017 | West et al. |
| 2017/0247743 | A1 | 8/2017 | Leung et al. |
| 2018/0003706 | A1 | 1/2018 | Trenholm et al. |
| 2018/0017580 | A1 | 1/2018 | Kaldate |
| 2018/0282376 | A1 | 10/2018 | Alter et al. |
| 2019/0017117 | A1 | 1/2019 | Barr et al. |
| 2019/0027249 | A1 | 1/2019 | Fuksenko et al. |
| 2019/0072557 | A1 | 3/2019 | Hill et al. |
| 2019/0101544 | A1 | 4/2019 | Danan-leon et al. |
| 2019/0113520 | A1 | 4/2019 | Blume et al. |
| 2019/0131016 | A1 | 5/2019 | Cohen et al. |

FOREIGN PATENT DOCUMENTS

| | | |
|---|---|---|
| CA | 2734535 A1 | 3/2010 |
| CA | 2769406 A1 | 2/2011 |
| CN | 100410663 C | 8/2008 |
| CN | 103278576 A | 9/2013 |

(56) References Cited

FOREIGN PATENT DOCUMENTS

| | | |
|---|---|---|
| EP | 1696237 A1 | 8/2006 |
| EP | 3035058 A1 | 6/2016 |
| JP | 2009057337 A | 3/2009 |
| JP | 2009168646 A | 7/2009 |
| JP | 2014027898 A | 2/2014 |
| TW | I426269 B | 2/2014 |
| WO | WO-2006020269 A2 | 2/2006 |
| WO | 2006121892 A2 | 11/2006 |
| WO | 2006121892 A3 | 2/2007 |
| WO | WO-2007144606 A2 | 12/2007 |
| WO | WO-2008047086 A2 | 4/2008 |
| WO | WO-2008108803 A2 | 9/2008 |
| WO | WO-2008149088 A2 | 12/2008 |
| WO | WO-2009075883 A2 | 6/2009 |
| WO | WO-2009117666 A1 | 9/2009 |
| WO | WO-2009138392 A1 | 11/2009 |
| WO | 2010096154 A2 | 8/2010 |
| WO | WO-2010144794 A1 | 12/2010 |
| WO | WO-2010144797 A2 | 12/2010 |
| WO | 2010096154 A3 | 1/2011 |
| WO | WO-2012016333 A1 | 2/2012 |
| WO | WO-2013192530 A2 | 12/2013 |
| WO | 2015009907 A1 | 1/2015 |
| WO | WO-2015023068 A1 | 2/2015 |
| WO | 2015200898 A1 | 12/2015 |
| WO | WO-2016030888 A1 | 3/2016 |
| WO | WO-2016036705 A1 | 3/2016 |
| WO | WO-2017149300 A1 | 9/2017 |
| WO | WO-2017190218 A1 | 11/2017 |
| WO | WO-2019079639 A1 | 4/2019 |
| WO | WO-2020160515 A1 | 8/2020 |

OTHER PUBLICATIONS

Aoshima et al., "A simple peak detection and label-free quantitation algorithm for chromatography-mass spectrometry", BMC bioinformatics 15(1):376; 14 pages (2014).

Barroso et al., "Classification of congenital disorders of glycosylation based on analysis of transferrin glycopeptides by capillary liquid chromatography-mass spectrometry", Talanta 160:614-623 (2016).

Cima et al., "Cancer genetics-guided discovery of serum biomarker signatures for diagnosis and prognosis of prostate cancer", Proceedings of the National Academy of Sciences of the United States of America 108(8): 3342-3347 (2011).

Datta et al., "Feature Selection And Machine Learning With Mass Spectrometry Data For Distinguishing Cancer And Non-Cancer Samples", Statistical Methodology 3: 79-92 (2006).

Demichev et al., "DIA-NN: Neural networks and interference correction enable deep coverage in high-throughput proteomics", bioRxiv, Oct. 25, 2018, XP055696494, DOI: 10.1101/282699; Retrieved from the Internet: URL:https://www.biorxiv.org/content/10.11.

Eshghi et al., "Quality assessment and interference detection in targeted mass spectrometry data using machine learning", Clinical Proteomics 15(33): 1-13 (2018).

Gallant et al., "Deconvolution of overlapping chromatographic peaks using a cerebellar model arithmetic C8computer neural network", Chemometrics And Intelligent Laboratory Systems, Elsevier Science Publishers B.V. Amsterdam, NL 18(1): 41-57 (1993).

Geng et al., "Proteomics of glycoproteins based on affinity selection of glycopeptides from tryptic digests", Journal of Chromatography B 752: 293-306 (2001).

Geurts et al., "Proteomic Mass Spectra Classification Using Decision Tree Based Ensemble Methods", Bioinformatics 21(15): 3138-3145 (2005).

He et al., "Liquid chromatography mass spectrometry-based 0-glycomics to evaluate glycosylation alterations in gastric cancer", Proteomics Clinical applications 10: 206-215 (2016).

Hilario et al., "Machine Learning Approaches To Lung Cancer Prediction From Mass Spectra", Proteomics 3: 1716-1719 (2003).

Hong et al., "Absolute Quantitation of Immunoglobulin G and Its Glycoforms Using Multiple Reaction Monitoring", Analytical Chemistry 85(18): 16 pages (2013).

Imre et al., "Mass spectrometric and linear discriminant analysis of N-glycans of human serum alpha-1-acid glycoprotein in cancer patients and healthy individuals", Journal of Proteomics 71(2):186-197 (2008).

Jeong et al., "Classification of core and outer fucosylation in N-glycoproteins by mass spectrometry with machine learning", Glycoconjugate Journal 34(Supplement 1): S91-S92 (2017).

Jinnelov et al., "Single-subunit oligosaccharyltransferases of Trypanosoma brucei display different and predictable peptide acceptor specificities", Journal of Biological Chemistry 292(49):20328-20341 (2017).

Joenvaara et al., "Quantitative N-glycoproteomics reveals altered glycosylation levels of various plasma proteins in bloodstream infected patients", PLOS ONE 13(3): e0195006 17 pages (2018).

Ju et al., "Elevated level of serum glycoprotein bifucosylation and prognostic value in Chinese breast cancer",Glycobiology 26(5):460-471 (2016).

Kaji et al., "Lectin Affinity Capture, Isotope-Coded Tagging and Mass Spectrometry to Identify N-linked Glycoproteins", Nature Biotechnology 21(6): 667-672 (2003).

Kiselyov et al., "VEGF/VEGFR signalling as a target for inhibiting angiogenesis", Expert Opin. Investig. Drugs 16(1):83-107 (2007).

Kumozaki et al., "A Machine learning based approach to de novo sequencing of glycans from tandem mass spectrometry spectrum", IEEE/ACM Transactions on Computational Biology and Bioinformatics 12(6): 1267-1274 (2015).

Le et al. "Identification of Serum Amyloid A as a Biomarker to Distinguish Prostate Cancer Patients with Bone Lesions", Clinical Chemistry 51(4): 695-707 (2005).

Levner, "Feature Selection and Nearest Centroid Classification For Protein Mass Spectrometry", BMC Bioinformatics 6(68): 14 pages (2005).

Li et al., "Site-Specific Glycosylation Quantitation of 50 Serum Glycoproteins Enhanced by Predictive Glycopeptidomics for Improved Disease Biomarker Discover", Analytical Chemistry 91(8): 5433-5445 (2019).

Liang et al., "An adaptive workflow coupled with Random Forest algorithm to identify intact N-glycopeptidesdetected from mass spectrometry", Bioinformatics 30(13): 1908-1916 (2014).

Liu et al., "Tandem 18O Stable Isotope Labeling for Quantification of N-Glycoproteome", Journal Of Proteome Research 9(1): 227-236 (2010).

MacLean et al., "Skyline: an open source document editor for creating and analyzing targeted proteomics experiments", Bioinformatics 26(7):966-968 (2010).

Neprasova et al., "Toward Noninvasive Diagnosis of IgA Nephropathy: A Pilot Urinary Metabolomic and Proteomic Study", Disease Markers, 2016, vol. 2016, Article ID 3650909: 9 pages (2016).

Noro et al., "Serum Aberrant N-Glycan Profile as a Marker Associated with Early Antibody-Mediated Rejection in Patients Receiving a Living Donor Kidney Transplant", Int. J. Molecular Sciences 18(8)1731: 17 pages (2017).

PCT/US2018/049256 International Search Report and Written Opinion dated Nov. 7, 2018.

PCT/US2018/056574 International Search Report and Written Opinion dated Jan. 3, 2019.

Tang et al., "Bioinformatics protocols in glycomics and glycoproteomics", Current Protocols in Protein Science Computational Analysis, Supplement 76, pp. 2.15.1-2.15.7 (2014).

Tang et al., "Identification of N-Glycan Serum Markers Associated with Hepatocellular Carcinoma from Mass Spectrometry Data", Journal of Proteome Research 9(1): 104-112 (2010).

Thompson et al., "Tandem Mass Tags: A Novel Quantification Strategy for Comparative Analysis of Complex Protein Mixtures by MS/MS", Anal. Chem. 75(8): 1895-1904 (2003).

Tran et al., "Deep learning enables de novo peptide sequencing from data-independent-acquisition mass spectrometry", Nature Methods 16(1): 63-66 (2018).

(56) References Cited

OTHER PUBLICATIONS

Wang et al., "Integrative Analysis of Proteomic, Glycomic, and Metabolomic Data for Biomarker Discovery", IEEE Journal of Biomedical and Health Informatics 20(5): 1225-1231 (2016).

Zhang et al., "Identification and quantification of N-linked glycoproteins using hydrazide chemistry, stable isotope labeling and mass spectrometry", Nature Biotechnology 21(6): 660-666 (2003).

Zohora et al., "DeepIso: A Deep Learning Model for Peptide Feature Detection from Lc-MS map ", Scientific Reports 9:171681 (2019).

Ahn, Y.H. et al. (2015, e-pub. Jun. 2, 2014). "Quantitative Mass Spectrometric Analysis of Glycoproteins Combined With Enrichment Methods," Mass Spectrometry Reviews 34(2):148-165.

Atkinson, K.R. (Jan. 1, 2008). "Proteomic Biomarker Discovery For Preeclampsia," Thesis of The University of Auckland, pp. 1-240.

Cho, J.W. et al. (Jul. 27, 2017). "GLYCO 24 International Symposium on Glycoconjugates," Glycoconjugate Journal 34(1):S1-S120.

Extended European Search Report, dated Sep. 13, 2021, for European Patent Application No. 18852234.6, 25 pages.

Hong, Q. et al. (Dec. 4, 2015). "A Method For Comprehensive Glycosite-Mapping and Direct Quantitation of Plasma Serum Glycoproteins," Journal of Proteome Research 14(12):5179-5192, 30 pages.

International Preliminary Report on Patentability, dated Mar. 3, 2020, for PCT Application No. PCT/US2018/049256, filed Aug. 31, 2018, 5 pages.

International Search Report and Written Opinion, dated Nov. 7, 2018 for PCT Application No. PCT/US2018/049256, filed Aug. 31, 2018, 7 pages.

Kawaguchi-Sakita, N. et al. (Jan. 22, 2016, e-pub. Dec. 29, 2015). "Serum Immunoglobulin G Fc Region N-glycosylation Profiling by Matrix-Assisted Laser Desorption/Ionization Mass Spectrometry Can Distinguish Breast Cancer Patients from Cancer-Free Controls," Biochemical and Biophysical Research Communications 469(4):1140-1145.

Maverakis, E. et al. (Feb. 2015, e-pub. Feb. 1, 2016). "Glycans In The Immune System and The Altered Glycan Theory of Autoimmunity: A Critical Review," Journal of Autoimmunity 57:1-13, 28 pages.

Mayampurath, A. et al. (Nov. 7, 2014, e-pub. Jul. 7, 2014). "Label-Free Glycopeptide Quantification for Biomarker Discovery in Human Sera," Journal of Proteome Research 13(11):4821-4832.

Ruhaak, L.R. et al. (Mar. 4, 2016, e-pub. Oct. 12, 2017). "Protein-Specific Differential Glycosylation of Immunoglobulins in Serum of Ovarian Cancer Patients," Journal of Proteome Research 15(3):1002-1010, 19 pages.

Shetty, V. et al. (Aug. 1, 2012). "Investigation of Ovarian Cancer Associated Sialylation Changes in N-Linked Glycopeptides by Quantitative Proteomics," Clinical Proteomics 9(1):10, 19 pages.

\* cited by examiner

IDENTIFICATION AND USE OF GLYCOPEPTIDES AS BIOMARKERS FOR DIAGNOSIS AND TREATMENT MONITORING

CROSS-REFERENCE TO RELATED APPLICATIONS

This application is a continuation of U.S. patent application Ser. No. 16/120,016, filed on Aug. 31, 2018, issued as U.S. Pat. No. 10,837,970 on Nov. 17, 2020, which claims priority to, and the benefit of, U.S. Provisional Patent Application No. 62/553,676, filed Sep. 1, 2017, each of which is hereby incorporated herein by reference in its entirety.

FIELD

The present disclosure relates generally to the field of multi-omics, in particular, glycomics and glycoproteomics, advanced instrumentation big data, machine learning and artificial intelligence to identify biomarkers for disease diagnosis and treatment monitoring.

BACKGROUND

Protein glycosylation and other post-translational modifications play vital structural and functional role in all aspects of human growth and development. Defective protein glycosylation accompanies several diseases. Identifying altered glycosylation at early disease stages provides opportunities for early detection, intervention and greater chance of survival in subjects affected. Currently, there are methods to identify biomarkers that can detect early cancer and discriminate a certain type of cancer from other diseases. Those methods include proteomics, peptidomics, metabolics, proteoglycomics and glycomics using mass spectrometry (MS).

Although protein glycosylation provides useful information about cancer and other diseases, one drawback of the method is that the glycan cannot be traced back to the protein site of origin. To gain more knowledge about cancer biology and an early detection of cancer, it is important not only to identify the glycan, but also its site of attachment within the protein. Glycoprotein analysis is challenging in general due to several reasons. For example, a single glycan composition in a peptide may contain a large number of isomeric structures because of different glycosidic linkages, branching and many monosaccharides having the same mass. Further, the presence of multiple glycans that share the same peptide backbone causes the MS signal to split into various glycoforms, lowering their individual abundances compared to the peptides that are not glycosylated. Therefore, it has been challenging to develop algorithms that can identify glycans and their peptides from the tandem MS data. It is also challenging to obtain comprehensive fragmentation for both the glycan and the peptide as they have different fragmentation efficiencies.

Thus, there is a need to provide a method for site-specific glycoprotein analysis to obtain crucial and detailed information about protein glycosylation patterns that provide precise quantitative information about the glycosylation site heterogeneity in diseased cells, tissues or bio-fluids compared with the non-diseased ones. Such a method will lead to identify disease biomarkers, particularly for diseases such as cancer. There is also a need to reduce the time in identifying new biomarkers by combining the site-specific glycoprotein analysis data with deep learning and advanced LC/MS instrumentation to identify and validate new disease targets, such as glycan-based drug targets, for diseases such as cancer.

SUMMARY

The present disclosure relates to methods of identifying biomarkers for various diseases. The biomarkers are the glycosylated peptide fragments obtained via fragmentation of glycosylated proteins from biological samples. The methods of identifying the biomarkers rely upon the use of advanced mass spectrometry techniques that allow for the accurate mass measurements of the glycosylated peptide fragments as well as the site-specific glycosylation analysis. The mass spectroscopy methods of the present disclosure are advantageously useful in analyzing a large number of glycosylated proteins from the biological samples at a time.

In one embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments.

In another embodiment, the method comprises the subjects having a disease or a condition and subjects not having the disease or the condition. In a further embodiment, the subjects comprise subjects receiving a treatment for a disease or a condition and subjects having the disease or the condition but not receiving a treatment.

In another embodiment, the methods of the present disclosure are applicable to any disease or condition that can be detected by analyzing the glycosylated peptide fragments from the biological samples of a subject. In one embodiment, the disease is cancer. In another embodiment, the disease is an autoimmune disease. In another embodiment, the methods of the present disclosure provide glycosylated peptide fragments that are O-glycosylated or N-glycosylated. In another embodiment, the methods of the present disclosure provide glycosylated peptide fragments having an average length of from 5 to 50 amino acid residues.

In another embodiment, the methods of the present disclosure employ glycosylated proteins that are one or more of alpha-1-acid glycoprotein, alpha-1-antitrypsin, alpha-1B-glycoprotein, alpha-2-HS-glycoprotein, alpha-2-macroglobulin, antithrombin-III, apolipoprotein B-100, apolipoprotein D, apolipoprotein F, beta-2-glycoprotein 1, ceruloplasmin, fetuin, fibrinogen, immunoglobulin (Ig) A, IgG, IgM, haptoglobin, hemopexin, histidine-rich glycoprotein, kininogen-1, serotransferrin, transferrin, vitronectin and zinc-alpha-2-glycoprotein.

In another embodiment, the methods of the present disclosure comprise fragmentation of the glycosylated proteins using at least two proteases. In another embodiment, the methods of the present disclosure employ LC-MS techniques using multiple reaction monitoring mass spectrometry (MRM-MS).

In another embodiment, the present disclosure provides methods for identifying glycosylated peptide fragments as potential biomarkers for various diseases as described herein, wherein the biological sample is body tissue, saliva, tears, sputum, spinal fluid, urine, synovial fluid, whole blood, serum or plasma obtained from the subjects. In one embodiment, the subjects are mammals. In another embodiment, the subjects are humans.

In another embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments, wherein the machine learning approach is deep learning, neural network, linear discriminant analysis, quadratic discriminant analysis, support vector machine, random forest, nearest neighbor or a combination thereof. In another embodiment, the machine learning approach is deep learning, neural network or a combination thereof.

In another embodiment, the present disclosure provides methods for identifying glycosylated peptide fragments as potential biomarkers for various diseases as described herein, wherein the analysis further comprises genomic data, proteomics, metabolics, lipidomics data, or a combination thereof.

DETAILED DESCRIPTION

Definitions

As used in the present specification, the following words and phrases are generally intended to have the meanings as set forth below, except to the extent that the context in which they are used indicates otherwise.

It is to be noted that as used herein and in the claims, the singular forms "a," "an" and "the" include plural referents unless the context clearly dictates otherwise.

The term "biological sample" refers to mean any biological fluid, cell, tissue, organ or a portion thereof. It also includes, but is not limited to, a tissue section obtained by biopsy, or cells that are placed in or adapted to tissue culture. It further includes, but is not limited to, saliva, tears, sputum, sweat, mucous, fecal material, gastric fluid, abdominal fluid, amniotic fluid, cyst fluid, peritoneal fluid, spinal fluid, urine, synovial fluid, whole blood, serum, plasma, pancreatic juice, breast milk, lung lavage, marrow, and the like.

The term "biomarker" refers to a distinctive biological or biologically-derived indicator of a process, event or a condition. A biomarker is also indicative of a certain biological state, such as presence of a disease or a condition or risk of a disease or a condition. It includes a biological molecule, or a fragment of a biological molecule, the change or detection of which can be correlated with a particular physical state or a condition. Example of biomarkers include, but are not limited to, biological molecules comprising nucleotides, amino acids, fatty acids, steroid, antibodies, hormones, steroids, peptides, proteins, carbohydrates, and the like. Further examples include glycosylated peptide fragments, lipoproteins, and the like.

The term "comprising" is intended to mean that the compositions and methods include the recited methods, but do not exclude others.

The term "glycan" refers to the carbohydrate portion of a glycoconjugate, such as a glycopeptide, glycoprotein, glycolipid or proteoglycan.

The term "glycoform" refers to a unique primary, secondary, tertiary and quaternary structure of a protein with an attached glycan of a specific structure.

The term "glycosylated peptide fragment" refers to a glycosylated peptide (or glycopeptide) having an amino acid sequence that is the same as part but not all of the amino acid sequence of the glycosylated protein from which the glycosylated peptide is obtained via fragmentation, e.g., with one or more proteases.

The term "multiple reaction monitoring mass spectrometry (MRM-MS)" refers to a highly sensitive and selective method for the targeted quantification of protein/peptide in biological samples. Unlike traditional mass spectrometry, MRM-MS is highly selective (targeted), allowing researchers to fine tune an instrument to specifically look for peptides/protein fragments of interest. MRM allows for greater sensitivity, specificity, speed and quantitation of peptides/protein fragments of interest, such as a potential biomarker. MRM-MS involves using a triple quadrupole (QQQ) mass spectrometer or quadrupole time-of-flight (qTOF) mass spectrometer.

The term "protease" refers to an enzyme that performs proteolysis or breakdown of proteins into smaller polypeptides or amino acids. Examples of a protease include, serine protease, threonine protease, cysteine protease, aspartate protease, glutamic acid protease, metalloprotease, asparagine peptide lyase and a combination thereof.

The term "subject" refers to a mammal. The non-liming examples of a mammal include a human, non-human primate, mouse, rat, dog, cat, horse, or cow, and the like. Mammals other than humans can be advantageously used as subjects that represent animal models of disease, pre-disease, or a pre-disease condition. A subject can be male or female. A subject can be one who has been previously identified as having a disease or a condition, and optionally has already undergone, or is undergoing, a therapeutic intervention for the disease or condition. Alternatively, a subject can also be one who has not been previously diagnosed as having a disease or a condition. For example, a subject can be one who exhibits one or more risk factors for a disease or a condition, or a subject who does not exhibit disease risk factors, or a subject who is asymptomatic for a disease or a condition. A subject can also be one who is suffering from or at risk of developing a disease or a condition.

The term "treatment" or "treating" means any treatment of a disease or condition in a subject, such as a mammal, including: 1) preventing or protecting against the disease or condition, that is, causing the clinical symptoms not to develop; 2) inhibiting the disease or condition, that is, arresting or suppressing the development of clinical symptoms; and/or 3) relieving the disease or condition that is, causing the regression of clinical symptoms.

Methods

Figure 1:
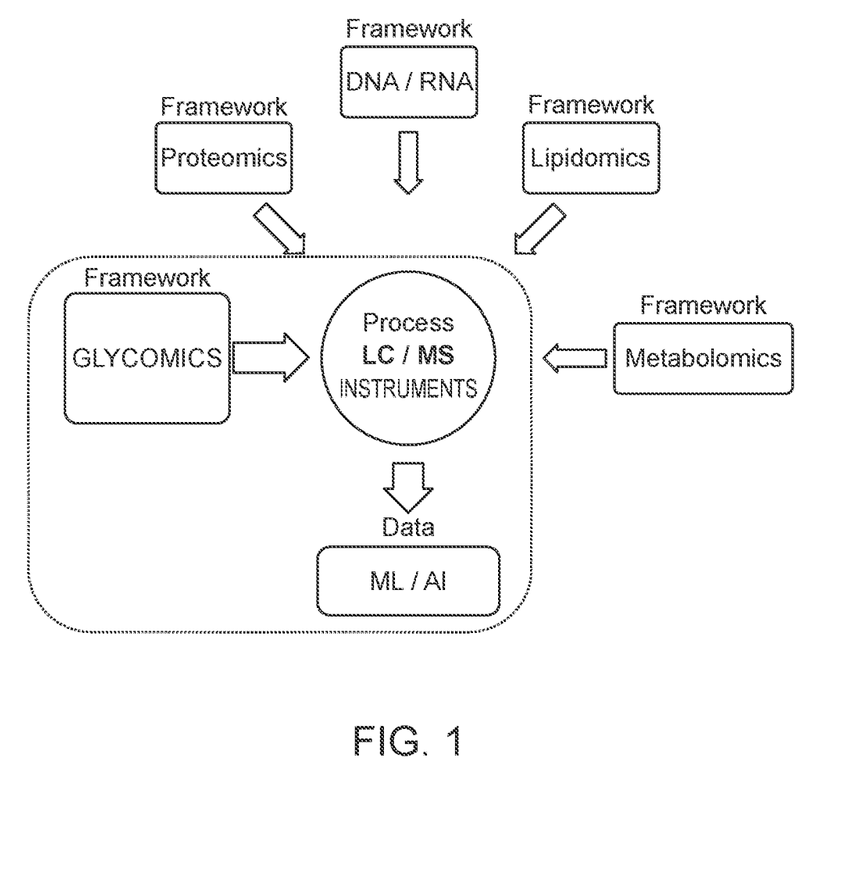
FIG. 1 is a Schematic diagram showing the integration of Glycomics, LC/MS and machine learning that can further be combined with proteomics, genomic, lipidomics and metabolics.

The present disclosure, in some embodiments, relates to glycoproteomics glycoproteomics for biomarker discovery, target discovery and validation using advanced LC/MS instrumentation. The disclosure utilizes machine learning methods to process the molecular data. The analysis further comprises utilizing genomic data, proteomics, metabolics, lipidomics data, or a combination thereof in discovering new biomarkers for various diseases. The general schematic for the methods of this disclosure is shown in FIG. 1.

The present disclosure provides methods for site-specific glycosylation analysis that leads to identification of new types of biomarkers with higher sensitivity and specificity. The method comprises quantitation of glycosylated peptides, thus facilitating differential analysis of distinct glycoforms associated with specific proteins at distinct sites. The method provides information regarding the amount of protein and the site-specific glycosylation profile, thus providing insight into whether the altered glycosylation profile is due to the change in protein glycosylation or it is due to a change in protein concentration. The site specific glycosylation analysis in combination with machine learning method(s) provide identification of new biomarkers for various diseases or conditions.

The quantitative glycoproteomics methods of the disclosure are used to discover biomarkers of various diseases. The methods are based on the fact that specific glycoforms are elevated and others are down regulated in several diseases and the LC/MS methods of the present disclosure differentiate between the disease versus no disease by analyzing the significant glycosylation changes. In one embodiment, the site-specific glycosylation analysis comprises identifying the glycoproteins of interest, the sites of modification, what the modification is and then measuring the relative abundance of each modification. In some embodiments, the disease is cancer. In other embodiments, the disease is an autoimmune disease.

Using the methods of this disclosure, the biological samples from thousands of subjects are digitized to generate tremendous amount of data that undergoes deep machine learning analysis to discover new targets for various diseases. Specifically, deep learning is used to compare clustering of known and unknown peptides and their glycosylation signatures as seen by LC/MS in disease versus control states. Such discriminant analysis of the glycosylated peptides leads to the identification of the disease biomarkers.

The identification of the biomarkers and their corresponding features such as their expression level are then used for developing diagnostic test methods for a disease or a condition, wherein the methods rely upon, at least in part, on measuring one or more of the selected biomarkers and analyzing the result for an association with the disease or the condition. The methods can further be used in selecting one or more therapies, determining a treatment regimen or to monitor response to a therapy for the particular disease or condition. Thus, the present disclosure provides methods for prevention, diagnosis, therapy, monitoring and prognosis of a disease or a condition. In some embodiments, the methods are useful in discriminating between the subjects having a disease or a condition and healthy subjects. In some embodiments, the methods are useful in discriminating between subjects having cancer and healthy subjects. In some embodiments, the methods are useful in aiding the diagnosis of cancer or for monitoring cancer.

Targeted and Non-Targeted Approaches

The biomarker discovery methods of the present disclosure employ both targeted and/or non-targeted approaches. The methods typically comprise three different phases, namely, discovery phase, pre-validation phase and validation phase.

Discovery Phase

The targeted approach comprises identifying and monitoring the known glycoproteins with their known glycoforms in the biological samples of subjects. There are known FDA approved glycoprotein biomarkers for various diseases and those are monitored using the methods of this disclosure to identify the classification of the subjects. Typically, the glycosylation changes of the biomarkers are tumor-specific and are useful in identifying a possible risk of the disease or a disease stage. The targeted approach focuses on the known glycoproteins and their glycoforms that are chemically characterized and biologically annotated with the established biological importance at the start of the study before data acquisition is performed. Quantification is performed through the use of internal standards and authentic chemical standards.

Specifically, in the targeted approach, the site-specific glycosylation analysis is conducted in biological samples from case-control study of a number of subjects having a disease or condition and equal number of matched control subjects not having the disease or condition. The glycoprotein of interest, such as a disease related glycoprotein or a glycoprotein with a biological activity, is first identified in the biological sample. It is then analyzed using LC/MS for the site of modification, nature of modification, identity of the modification and the relative abundance of each modification, leading to identification and quantification of the peptide fragments. This approach uses triple quadrupole (QQQ) mass spectrometer for the quantification of the glycosylated peptide fragments which are then analyzed for its relation to the classification of the subjects.

The non-targeted approach comprises learning the glycosylation patterns of known as well as unknown peptide fragments to provide more information on changes in glycosylation patterns that is useful in identifying the classification of the subjects. The non-targeted approach is based on relative quantitation technique that provides "up or down regulation" of the glycoproteins. Specifically, the up or down regulation of the glycoproteins is monitored in relation to the classification of the subjects. For example, the glycoprotein fragments are monitored for subjects having a disease or a condition versus subjects not having a disease or a condition. This approach does not know the chemical identity of each glycoprotein fragment before the data is acquired. In one embodiment, the non-targeted approach uses quadrupole time-of-flight (qTOF) mass spectrometer for the analysis of the glycosylated peptide fragments. This approach involves using the instrumentation to accurately measure the mass of components in a sample, without any preconceived notion about what those components might be.

The candidates differently expressed between the groups (disease vs. no disease) are selected for further evaluation, using machine learning methods to allow for the prediction of classification with feature selection techniques with important clinical characteristics. Performance is evaluated using internal cross validation in which features are selected and models are constructed using the training set. The resulting models are evaluated on the test set that was not used in the construction of the model. The false positive rate is controlled by using the false discovery rate (FDR) approach introduced by Benjamin and Hochberg.

Pre-Validation Phase

The candidate biomarkers thus identified in the discovery phase are then tested in an independent test set of biological samples obtained from a number of subjects having a disease or a condition and their matched controls not having the disease or condition, to determine the performance of the candidate biomarkers. The selected biomarker, its ranking, together with any parameter estimation of the models developed in the discovery phase are all part of the modelling and are tested with this independent pre-validation phase. According to the signals of candidate biomarkers, a diagnostic test classifies the biological samples into two groups: those with a disease and those without a disease. The test is then assessed for its usefulness based on positive predictive value, negative predictive value, specificity and sensitivity. Also, the diagnostic performance is evaluated using receiver operating characteristic (ROC) curves to test which biomarkers or a combination of multiple biomarkers are statistically better diagnostic tests for a disease or condition. The individual biomarkers that are successfully validated are examined for subsequent inclusion to form a panel of composite markers. The composite markers are constructed by weighted multi-variable logistic regression or other classification algorithms.

Validation Phase

The candidate biomarkers retained in the pre-validation phase are then validated through independent validations using independent blinded biological samples from a number of subjects. The purpose of this phase is to assess the diagnostic precision of the selected biomarkers.

In one embodiment, the biomarker discovery method is applied to biological samples obtained from subjects having cancer. In some embodiments, biological samples from at least 20, at least 40, at least 60, at least 80 or at least 100 subjects are analyzed in each group (i.e. a group having cancer or a group not having cancer).

Both targeted and/or non-targeted approaches, along with the machine learning methods as described herein, provide new diagnostic methods for identifying possible risk and/or early stage detection of various diseases. In one embodiment, this disclosure provides the methods of identification of biomarkers that are based on the convergence of targeted and non-targeted approaches in combination with the machine learning method. The biomarkers identified by the methods of the present disclosure are useful in methods of diagnosis, methods of prognosis assessment, monitoring results of therapy, identifying subjects likely to respond to a particular treatment, drug screening, and the like.

In one embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments.

In another embodiment, the present disclosure provides the method as described herein, wherein subjects comprise subjects having a disease or condition and subjects not having the disease or condition. In a further embodiment, the subjects comprise subjects receiving a treatment for a disease and subjects having the disease but not receiving a treatment for the disease.

The methods of the present disclosure are applicable to any disease or condition that can be detected by analyzing the glycosylated peptide fragments from the biological samples of a subject. In one embodiment, the disease is cancer. In another embodiment, the cancer selected from breast cancer, cervical cancer or ovarian cancer. In another embodiment, the disease is an autoimmune disease. In another embodiment, the autoimmune disease is HIV, primary sclerosing cholangitis, primary biliary cirrhosis or psoriasis.

In another embodiment, the present disclosure provides the methods as described herein, wherein the glycosylated proteins are one or more of alpha-1-acid glycoprotein, alpha-1-antitrypsin, alpha-1B-glycoprotein, alpha-2-HS-glycoprotein, alpha-2-macroglobulin, antithrombin-III, apolipoprotein B-100, apolipoprotein D, apolipoprotein F, beta-2-glycoprotein 1, ceruloplasmin, fetuin, fibrinogen, immunoglobulin (Ig) A, IgG, IgM, haptoglobin, hemopexin, histidine-rich glycoprotein, kininogen-1, serotransferrin, transferrin, vitronectin and zinc-alpha-2-glycoprotein. In another embodiment, the glycosylated proteins are one or more of alpha-1-acid glycoprotein, immunoglobulin (Ig) A, IgG or IgM.

In another embodiment, the present disclosure provides the methods as described herein, wherein the glycosylated peptide fragment is N-glycosylated or O-glycosylated.

In another embodiment, the present disclosure provides the methods as described herein, wherein the glycosylated peptide fragments have an average length of from about 5 to about 50 amino acid residues. In some embodiments, the glycosylated peptide fragments have an average length of from about 5 to about 45, or from about 5 to about 40, or from about 5 to about 35, or from about 5 to about 30, or about from 5 to about 25, or from about 5 to about 20, or from about 5 to about 15, or from about 5 to about 10, or from about 10 to about 50, or from about 10 to about 45, or from about 10 to about 40, or from about 10 to about 35, or from about 10 to about 30, or from about 10 to about 25, or from about 10 to about 20, or from about 10 to about 15, or from about 15 to about 45, or from about 15 to about 40, or from about 15 to about 35, or from about 15 to about 30, or about from 15 to about 25 or from about 15 to about 20 amino acid residues. In one embodiment, the glycosylated peptide fragments have an average length of about 15 amino acid residues. In another embodiment, the glycosylated peptide fragments have an average length of about 10 amino acid residues. In another embodiment, the glycosylated peptide fragments have an average length of about 5 amino acid residues.

In another embodiment, the present disclosure provides the methods as described herein, wherein the one or more proteases comprise any protease that is used for fragmenting proteins. In one embodiment, the protease is a serine protease, threonine protease, cysteine protease, aspartate protease, glutamic acid protease, metalloprotease, asparagine peptide lyase or a combination thereof. A few representative examples of a protease include, but are not limited to, trypsin, chymotrypsin, endoproteinase, Asp-N, Arg-C, Glu-C, Lys-C, pepsin, thermolysin, elastase, papain, proteinase K, subtilisin, clostripain, carboxypeptidase and the like. In another embodiment, the present disclosure provides the methods as described herein, wherein the one or more proteases comprise at least two proteases.

The methods of the present disclosure have several further applications. For example, the one of more biomarkers are useful to discriminate between the pre-disease state from a disease state, or a disease state from a normal state. Other non-disease specific health states can also be determined. For example, changes of the biomarker can be assayed at different times: in a subject with a disease, to monitor the progress of the disease; in a subject undergoing treatment, to monitor the effect of the treatment and in a subject post-treatment, to monitor a possible relapse. Also, the levels of a specific amount of biomarker also may allow for choosing the course of treatment of the disease. For example, a biological sample can be provided from a subject undergoing treatment regimens for a disease. Such treatment regimens can include, but are not limited to, exercise regimens, dietary supplementation, weight loss, surgical intervention, device implantation, and treatment with therapeutics or prophylactics used in subjects diagnosed or identified with a disease or condition.

Moreover, changes in glycopeptide ratios in a plurality of glycoproteins can be associated with a certain disease state or absence of a disease. For example, presence of a plurality of particular glycopeptides in a biological sample may indicate absence of a disease, whereas presence of a plurality of other specific glycopeptides in a biological sample may indicate presence of the disease. Thus, various glycopeptide profiles or panels of glycopeptide biomarkers can be correlated with various states of a disease.

Figure 2:
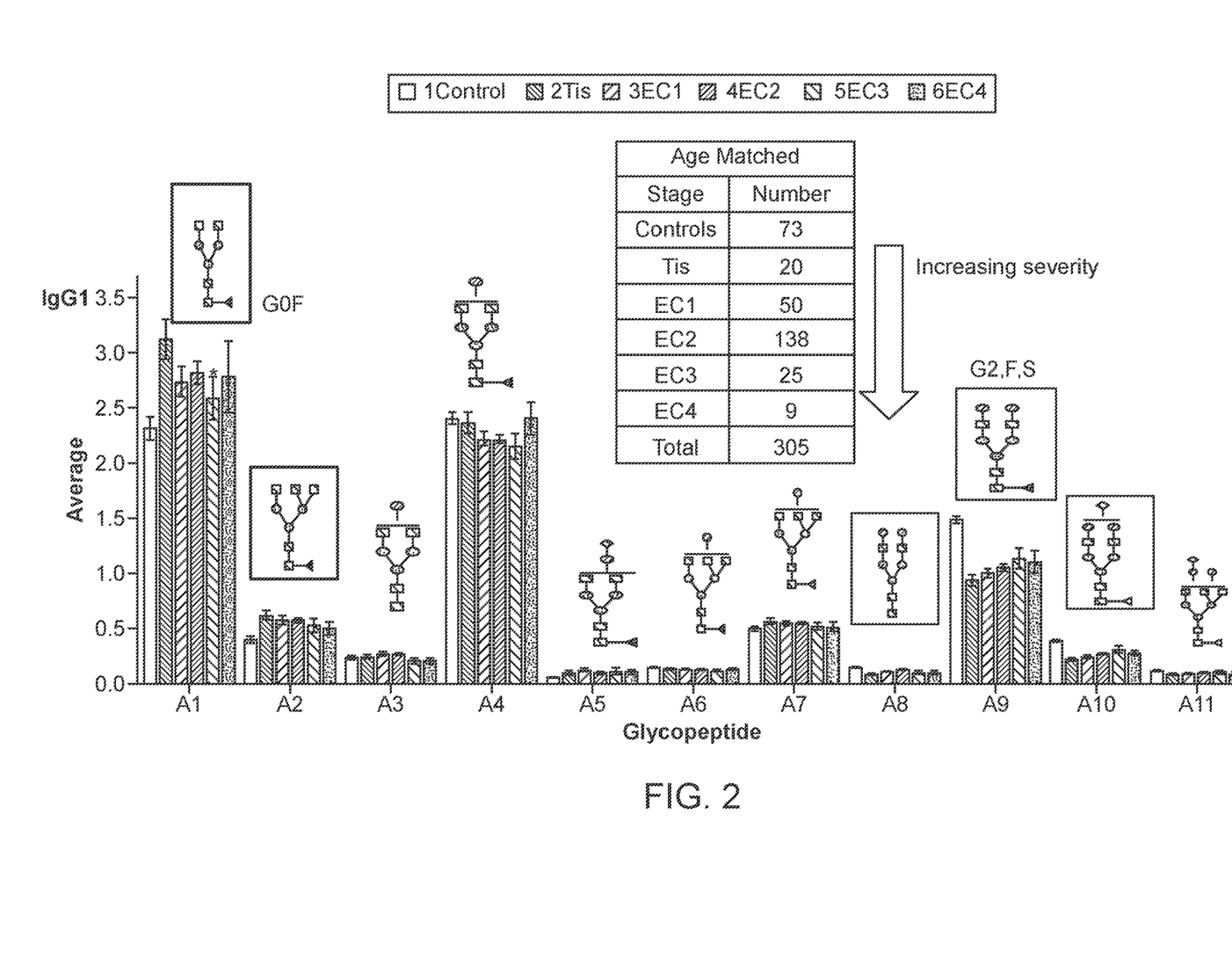
FIG. 2 shows changes in immunoglobulin G (IgG) glycopeptide ratios in plasma samples from breast cancer patients versus controls.

Example 2 shows quantitation results of changes in IgG1, IgG0 and IgG2 glycopeptides in plasma samples from breast cancer patients versus the controls. FIG. 2 illustrates that the levels of glycopeptides A1 and A2 were elevated as compared to the control, whereas the levels of glycopeptides A8, A9 and A10 were reduced as compared to the control in all stages of breast cancer studied in this experiment, thus indicating that glycopeptides A1, A2, A8, A9 and A10 are potential biomarkers for breast cancer.

Figure 3:
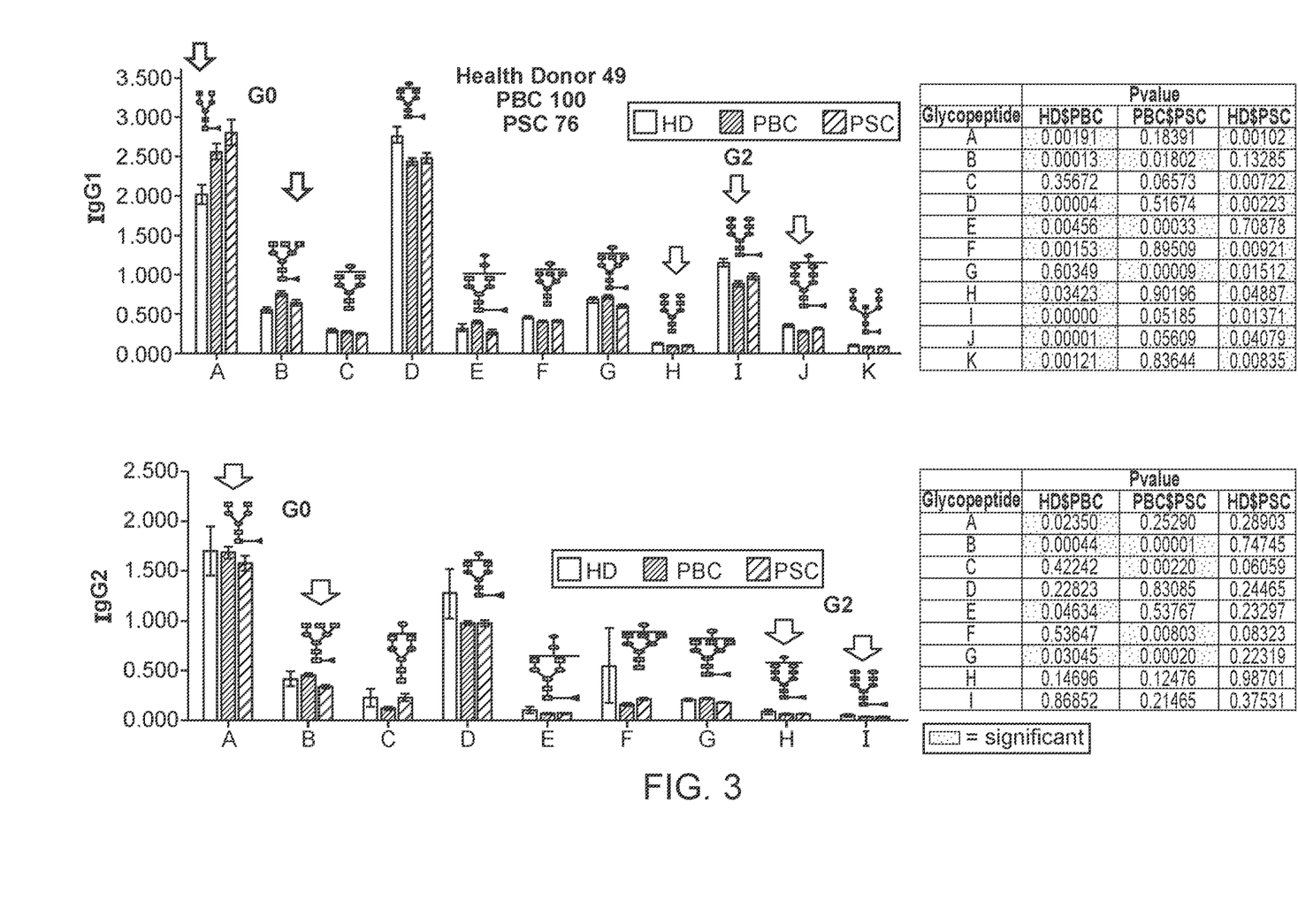
FIG. 3 shows changes in IgG glycopeptide ratios in plasma samples from primary sclerosing cholangitis (PSC) and primary biliary cirrhosis (PBC) samples versus healthy donors.
Figure 4:
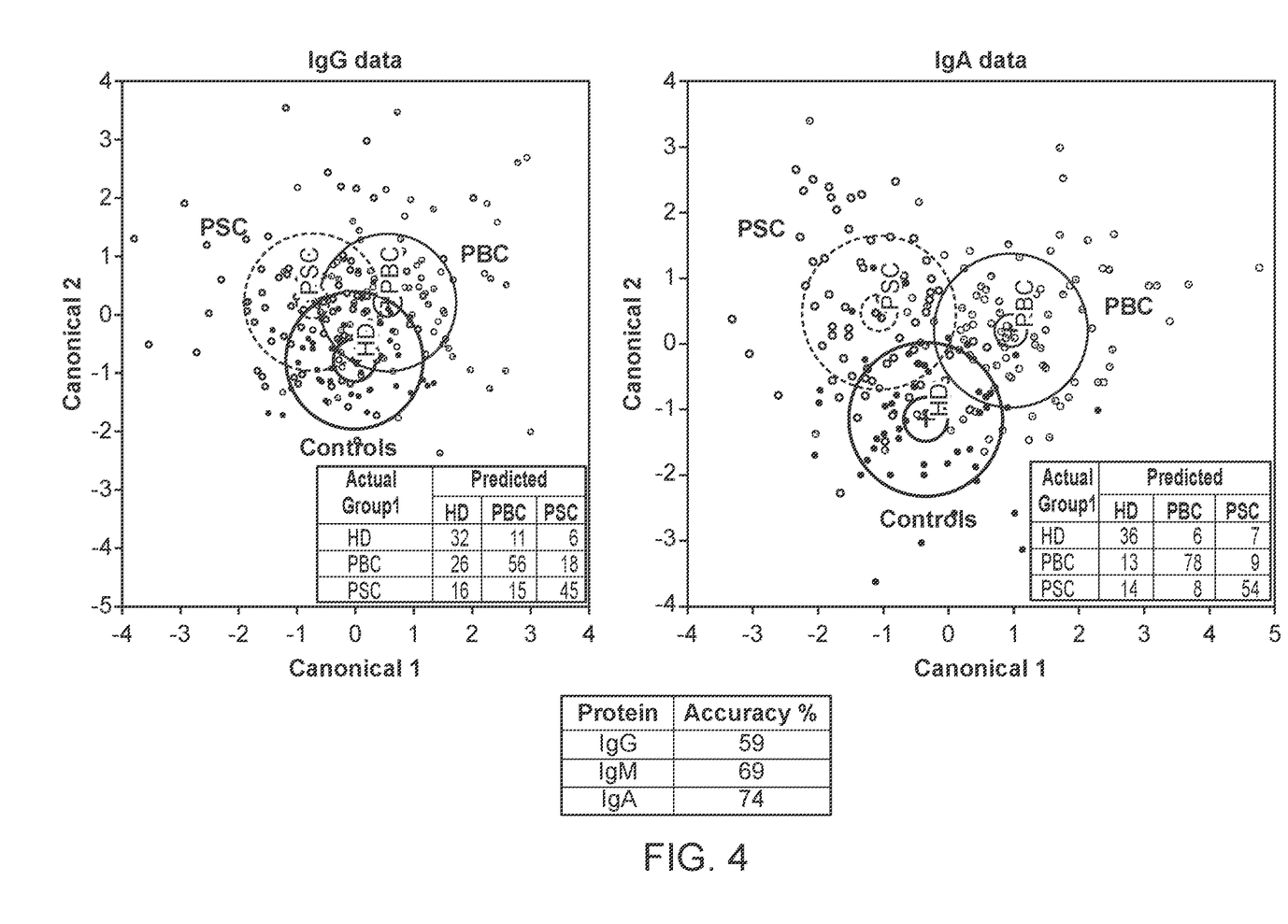
FIG. 4 shows the separate discriminant analysis data for IgG, IgA and IgM glycopeptides in plasma samples from PSC and PBC samples versus healthy donors.

Example 3 shows quantification results of changes in IgG, IgM and IgA glycopeptides in plasma samples from patients having PSC and patients having PSC. FIG. 3 illustrates that glycopeptide A was elevated as compared to the healthy donors in plasma samples of patients having PBC and PSC, whereas glycopeptides H, I and J were reduced as compared to the healthy donors in plasma samples of patients having PBC and PSC. Thus, glycopeptides A, H, I and J are potential biomarkers for PBC and PSC. Further, the separate and combined discriminant analysis results are provided in FIG. 4 and FIG. 5 respectively indicating an accuracy of 88% for predicting the disease state in the combined discriminant analysis.

In some embodiments, the present disclosure provides methods, wherein the number of biomarkers that are detected and analyzed are 1, or more than 1, such as 2, 3, 4, 5, 6, 7, 8, 9, 10, 11, 12, 13, 14, 15, 16, 17, 18, 19 20, 21, 22, 23, 24, 25, 26, 27, 28, 30 or more. Thus, the disclosure also provides a panel of biomarkers that is useful in the diagnosis of a disease or condition.

Mass Spectroscopy

In one embodiment, the present disclosure provides methods as described herein that comprise quantitating the glycosylated peptide fragments by using a mass spectrometer. In one embodiment, the methods employ a technique called "multiple reaction monitoring (MRM)." This technique is often coupled with liquid chromatography (LC/MRM-MS) and allows the quantitation of hundreds of glycosylated peptide fragments (and their parent proteins) in a single LC/MRM-MS analysis. The advanced mass spectroscopy techniques of the present disclosure provide effective ion sources, higher resolution, faster separations and detectors with higher dynamic ranges that allow for broad untargeted measurements that also retain the benefits of targeted measurements.

The mass spectroscopy methods of the present disclosure are applicable to several glycosylated proteins at a time. For example, at least more than 50, or at least more than 60 or at least more than 70, or at least more than 80, or at least more than 90, or at least more than 100, or at least more than 110 or at least more than 120 glycosylated proteins can be analyzed at a time using the mass spectrometer.

In one embodiment, the mass spectroscopy methods of the present disclosure employ QQQ or qTOF mass spectrometer. In another embodiment, the mass spectroscopy methods of the present disclosure provide data with high mass accuracy of 10 ppm or better; or 5 ppm or better; or 2 ppm or better; or 1 ppm or better; or 0.5 ppm or better; or 0.2 ppm or better or 0.1 ppm or better at a resolving power of 5,000 or better; or 10,000 or better; or 25,000 or better; or 50,000 or better or 100,000 or better.

Biological Samples

The present disclosure provides methods that are based on quantitating the glycosylated peptide fragments from biological samples. In some embodiments, the biological samples are one or more clinical samples collected in the past, thus reducing the resources and time that must be committed to identifying new biomarkers. In some embodiments, the biological samples are from one or more past studies that occurred over a span of 1 to 50 years or more. In some embodiments, the studies are accompanied by various other clinical parameters and previously known information such as the subject's age, height, weight, ethnicity, medical history, and the like. Such additional information can be useful in associating the subject with a disease or a condition. In some embodiments, the biological samples are one or more clinical samples collected prospectively from the subjects.

In one embodiment, the present disclosure provides the methods as described herein, wherein the biological sample isolated from the subjects is one or more of saliva, tears, sputum, sweat, mucous, fecal material, gastric fluid, abdominal fluid, amniotic fluid, cyst fluid, peritoneal fluid, spinal fluid, urine, synovial fluid, whole blood, serum, plasma, pancreatic juice, breast milk, lung lavage, marrow. In another embodiment, the biological sample isolated from the subjects is body tissue, saliva, tears, sputum, spinal fluid, urine, synovial fluid, whole blood, serum or plasma. In another embodiment, the biological sample isolated from the subjects is whole blood, serum or plasma. In some embodiments, the subjects are mammals. In other embodiments, the subject are humans.

Diseases

The methods of the present disclosure are applicable to any disease or condition that can be detected by analyzing the glycosylated peptide fragments from the biological samples of a subject. In some embodiments, the disease or condition is cancer. In other embodiments, the cancer is acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CIVIL), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, testicular cancer, thyroid cancer, urinary system cancer, uterine sarcoma, vaginal cancer, vascular system, Waldenstrom's macroglobulinemia, Wilms' tumor, and the like. In another embodiment, the cancer is breast cancer, cervical cancer or ovarian cancer.

In another embodiment, the disease is an autoimmune disease. In another embodiment, the autoimmune disease is acute disseminated encephalomyelitis, Addison's disease, agammaglobulinemia, age-related macular degeneration, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune uticaria, autoimmune uveitis, Balo disease/Balo concentric sclerosis, Behcet's disease, Berger's disease, Bickerstaff's encephalitis, Blau syndrome, Bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, glomerulonephritis, Goodpasture's syndrome, Graves' disease, Guillan-Barre syndrome, Hashimoto's encephalopathy, Hashimoto's thyroiditis, Henoch-Schonlein purpura, HIV, gestational pemphigoid, hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, multiple sclerosis, myasthenia gravis, myositis, narcolepsy, neuromyelitis optica, neuromyotonia, occular cicatricial pemphigoid, opsoclonus myoclonus syndrome, Ord's thyroiditis, palindromic rheumatism, pediatric autoimmune neuropsychiatric disorders associated with *Streptococcus*, paraneoplastic cerebellar degeneration, paroxysmal nocturnal hemoglobinuria, Parry Romberg syndrome, Parsonage-Turner syndrome, Pars planitis, pemphigus vulgaris, pernicious anemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjogren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, urticarial vasculitis, vasculitis, vitiligo and Wegener's granulomatosis, and the like. In another embodiment, the autoimmune disease is HIV, primary sclerosing cholangitis, primary biliary cirrhosis or psoriasis.

Machine Learning

The biological samples are obtained from thousands of subjects which are then used for digitizing with the intention of deep mining for and validating previously undiscovered markers. In some embodiments, the biological samples are tumor samples or blood samples. They are digitized using LC/MS instruments to generate tremendous amount of data that undergoes deep machine learning analysis to discover new targets for various diseases. In some embodiments, the disease is cancer or autoimmune disease.

In one embodiment, the present disclosure provides a method for identifying glycosylated peptide fragments as potential biomarkers, comprising:

fragmenting glycosylated proteins in each of a plurality of biological samples isolated from subjects, with one or more proteases, to produce glycosylated peptide fragments;

quantitating the glycosylated peptide fragments with liquid chromatography and mass spectrometry (LC-MS) to provide quantitation results;

analyzing the quantitation results along with classification of the subjects with a machine learning method to select glycosylated peptide fragments useful for predicting the classification; and determining the identity of glycosylated peptide fragments, wherein the machine learning approach is deep learning, neural network, linear discriminant analysis, quadratic discriminant analysis, support vector machine, random forest, nearest neighbor or a combination thereof. In some embodiments, the machine learning approach is deep learning, neural network or a combination thereof. The analysis further comprises genomic data, proteomics, metabolics, lipidomics data, or a combination thereof. FIG. 1 displays a Schematic diagram showing the integration of Glycomics, LC/MS and machine learning that is further combined with proteomics, genomic, lipidomics and metabolics to identify the biomarkers for various diseases.

EXAMPLES

Example 1

General Method for Biomarker Discovery

In the targeted approach, the glycoprotein of interest, is first identified in the biological sample and then analyzed using LC/MS for the site of modification, nature of modification, identity of the modification and the relative abundance of each modification, leading to identification and quantification of the peptide fragments. This approach uses triple quadrupole (QQQ) mass spectrometer for the quantification of the glycosylated peptide fragments which is then analyzed for its relation to the classification of the subjects.

In the non-targeted approach, the glycosylation patterns of all peptide fragments (known as well as unknown) are analyzed to information on changes in glycosylation patterns in various subjects. Specifically, the up or down regulation of the glycoproteins is monitored in relation to the classification of the subjects. For example, the glycoprotein fragments are monitored for subjects having a disease or a condition versus subjects not having a disease or a condition. This approach uses quadrupole time-of-flight (qTOF) mass spectrometer for the analysis of the glycosylated peptide fragments.

Example 2

Quantification of IgG Glycopeptides as Potential Biomarkers for Breast Cancer

Plasma samples from breast cancer patients having various stages of cancer and their aged matched controls were analyzed for the IgG1, IgG0 and IgG2 glycopeptides and the changes in their ratios were compared. Specifically, 20 samples in Tis stage, 50 samples in EC1 stage, samples in EC2 stage, 25 samples in EC3 stage, 9 samples in EC4 stage and their 73 age matched control samples were subjected to MRM quantitative analysis on a QQQ mass spectrometer. As can be seen from the quantitative results in FIG. 2, the levels of certain IgG1 glycopeptides were elevated as compared to the controls, whereas the levels of certain IgG1 glycopeptides were reduced as compared to the controls in all stages of breast cancer studied in this experiment. See for example, IgG1 glycopeptides named as A1-A11, were monitored and it was found that the levels of glycopeptides A1 and A2 were elevated as compared to the control, whereas the levels of glycopeptides A8, A9 and A10 were reduced as compared to the control in all stages of breast cancer studied in this experiment. Thus, glycopeptides A1, A2, A8, A9 and A10 are potential biomarkers for breast cancer.

Example 3

Quantification of IgG Glycopeptides as Potential Biomarkers for PSC and PBC

Plasma samples from patients having primary sclerosing cholangitis (PSC), patients having primary biliary cirrhosis (PBC) and plasma samples from healthy donors were analyzed for IgG1 and IgG2 glycopeptides and the changes in their glycopeptide ratios were compared. Specifically, 100 PBC plasma samples, 76 PSC plasma samples and plasma samples from 49 healthy donors were subjected to MRM quantitative analysis on a QQQ mass spectrometer. As can be seen from the quantitative results in FIG. 3, certain IgG1 glycopeptides were elevated as compared to the healthy donors, whereas certain IgG1 glycopeptides were reduced as compared to the controls in plasma samples of patients having PBC and PSC. See for example, glycopeptide A was elevated as compared to the healthy donors in patients having PBC and PSC, whereas glycopeptides H, I and J were reduced as compared to the healthy donors in plasma samples of patients having PBC and PSC. Thus, glycopeptides A, H, I and J are potential biomarkers for PBC and PSC.

Figure 5:
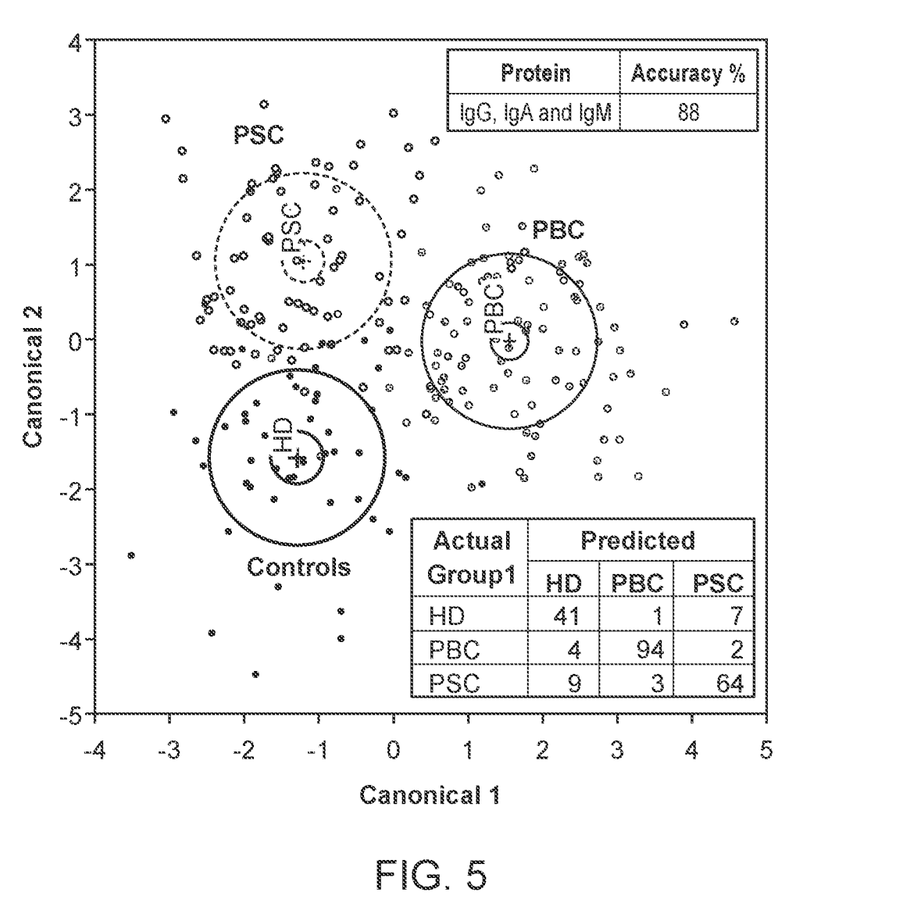
FIG. 5 shows the combined discriminant analysis data for IgG, IgA and IgM glycopeptides in plasma samples from PSC and PBC patients versus healthy donors.

Similar analysis was carried out on IgA and IgM glycoproteins in plasma samples of patients having PBC and plasma samples of patients having PSC. The discriminant analysis results are provided in FIG. 4 which indicate the % accuracy that can be predicted based on the separate data on IgG, IgM and IgA is 59%, 69% and 74% respectively. However, when the results are combined for all IgG, IgM and IgA, the discriminant analysis provides an accuracy of about 88% as shown in FIG. 5.

What is claimed is:

1. A method for determining a condition-associated site-specific glycosylation profile, the method comprising:
   (a) subjecting each of a plurality of biological samples to one or more proteases to produce a set of respective protease-processed samples,
      wherein each of the plurality of biological samples is from a human subject having a classification assigned based on having a condition or not having the condition, and
      wherein the plurality of biological samples comprises samples from human subjects having the condition and human subjects not having the condition;
   (b) subjecting each protease-processed sample to a liquid chromatography multiple reaction monitoring mass spectrometry (LC-MRM-MS) technique configured to selectively interrogate target species of interest,
      wherein the target species of interest comprise a plurality of glycopeptides and glycoforms thereof associated with at least more than 50 glycoproteins;
   (c) analyzing the information obtained from the LC-MRM-MS technique to produce quantitation results for each protease-processed sample; and
   (d) subjecting the quantitation results of each protease-processed sample along with the associated classification to a machine learning method to determine the condition-associated site-specific glycosylation profile.

2. The method of claim 1, wherein the condition is cancer.

3. The method of claim 2, wherein the cancer is breast cancer, cervical cancer, or ovarian cancer.

4. The method of claim 1, wherein the condition is an autoimmune disease.

5. The method of claim 1, wherein the target species of interest comprise glycopeptides and glycoforms from one or more of alpha-1-acid glycoprotein, alpha-1-antitrypsin, alpha-1B-glycoprotein, alpha-2-HS-glycoprotein, alpha-2-macroglobulin, antithrombin-III, apolipoprotein B-100, apolipoprotein D, apolipoprotein F, beta-2-glycoprotein 1, ceruloplasmin, fetuin, fibrinogen, immunoglobulin (Ig) A, IgG, IgM, haptoglobin, hemopexin, histidine-rich glycoprotein, kininogen-1, serotransferrin, transferrin, and vitronectin zinc-alpha-2-glycoprotein.

6. The method of claim 5, wherein the target species of interest comprise glycopeptides and glycoforms from one or more of immunoglobulin (Ig) A, IgG, and IgM.

7. The method of claim 1, wherein the one or more proteases comprise a serine protease.

8. The method of claim 1, wherein the plurality of biological samples are each selected from the group consisting of a whole blood sample, serum sample, and plasma sample.

9. The method of claim 1, wherein the machine learning method comprises a deep learning, neural network, discriminant analysis, support vector machine, random forest, nearest neighbor algorithm, or a combination thereof.

10. The method of claim 9, wherein the machine learning method comprises the deep learning, neural network algorithm, or a combination thereof.

11. The method of claim 1, further comprising identifying one or more glycopeptides and glycoforms thereof indicative of the condition-associated site-specific glycosylation profile.

12. The method of claim 2, wherein the cancer is breast cancer.

13. The method of claim 4, wherein the autoimmune disease is HIV infection-associated autoimmune disease, primary sclerosing cholangitis, primary biliary cirrhosis, or psoriasis.

14. The method of claim 13, wherein the autoimmune disease is primary biliary cholangitis or primary biliary cirrhosis.

15. The method of claim 1, wherein the human subjects not having the condition are healthy donors.

16. The method of claim 8, wherein the plurality of biological samples are whole blood samples.

17. The method of claim 8, wherein the plurality of biological samples are serum samples.

18. The method of claim 8, wherein the plurality of biological samples are plasma samples.

19. The method of claim 1, wherein the LC-MRM-MS technique is performed on a triple quadrupole mass spectrometer.

20. The method of claim 19, wherein the triple quadrupole mass spectrometer has a mass accuracy of 10 ppm or better.

21. The method of claim 7, wherein the serine protease is selected from the group consisting of trypsin, chymotrypsin, endoproteinase, Arg-C, Glu-C, Lys-C, and proteinase K.

22. The method of claim 6, wherein the quantitation results comprising information from IgG, IgA, and IgM glycopeptides and glycoforms of each protease-processed sample along with the associated classification are subjected to a machine learning method comprising a combined discriminant analysis.

23. The method of claim 1, wherein the plurality of biological samples comprises samples from at least 20 human subjects having the condition and at least 20 human subjects not having the condition.

24. The method of claim 1, wherein the plurality of biological samples comprises samples from at least 40 human subjects having the condition and at least 40 human subjects not having the condition.

* * * * *

UNITED STATES PATENT AND TRADEMARK OFFICE
CERTIFICATE OF CORRECTION

| | | |
|---|---|---|
| PATENT NO. | : 11,624,750 B2 | Page 1 of 1 |
| APPLICATION NO. | : 17/067460 | |
| DATED | : April 11, 2023 | |
| INVENTOR(S) | : Carrascoso et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 165 days.

Signed and Sealed this
Twentieth Day of May, 2025

Coke Morgan Stewart
*Acting Director of the United States Patent and Trademark Office*